United States Patent [19]
Confer

[11] 3,997,416
[45] Dec. 14, 1976

[54] METHOD AND APPARATUS FOR ANALYZING GASEOUS MIXTURES

[75] Inventor: Robert G. Confer, Colonia, N.J.

[73] Assignee: Exxon Research and Engineering Company, Linden, N.J.

[22] Filed: Sept. 20, 1974

[21] Appl. No.: 507,775

[52] U.S. Cl. .................... 23/232 E; 23/254 E; 23/232 R; 23/254 R
[51] Int. Cl.² ..................................... G01N 33/00
[58] Field of Search ............... 23/232 R, 254 R; 204/158 R, 157.1 R, 195 R, 232 E, 254 E; 250/527; 324/30 R, 71 R

[56] References Cited
UNITED STATES PATENTS

| 2,541,578 | 10/1975 | Egalon et al. | 204/195 R |
| 3,926,560 | 12/1975 | Gentry | 23/232 E |

*Primary Examiner*—Howard S. Williams
*Attorney, Agent, or Firm*—Harold N. Wells; F. Donald Paris

[57] ABSTRACT

A method and apparatus for analyzing gaseous mixtures by decomposing predetermined components of a sample of the mixture with ultraviolet radiation and thereafter measuring the amount of decomposition products produced as an indirect determination of the composition of the original sample. In one embodiment, the apparatus can measure the presence of less than one part per million of vinyl chloride in air by scrubbing a sample of gas to remove interfering compounds, decomposing the vinyl chloride by exposure to ultraviolet radiation, measuring the decomposition products by absorbing them in deionized water, and determining the change in electrical conductivity of the resulting solution as a measure of the amount of vinyl chloride in the sample.

10 Claims, 2 Drawing Figures

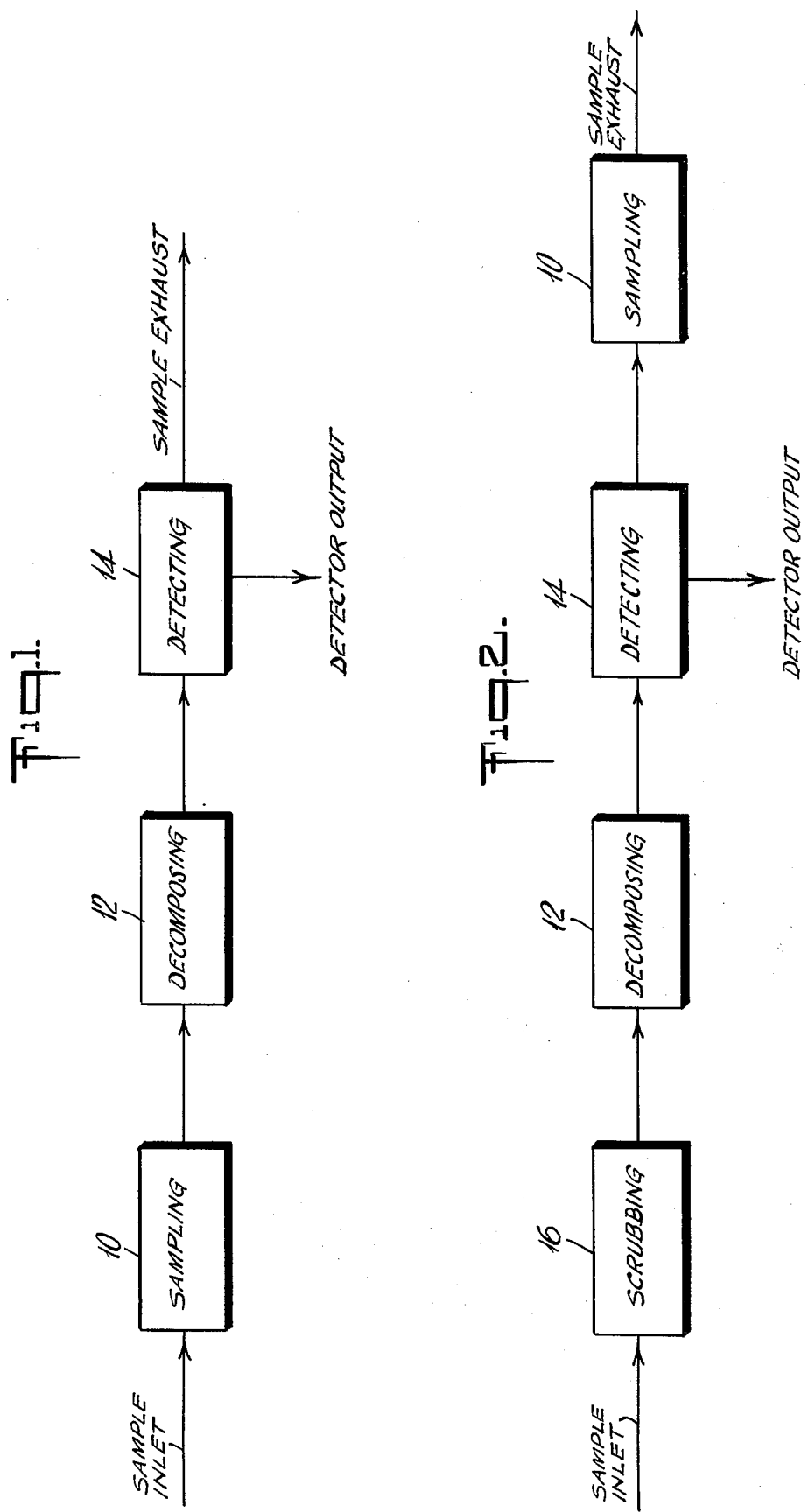

METHOD AND APPARATUS FOR ANALYZING GASEOUS MIXTURES

BACKGROUND OF THE INVENTION

This invention relates broadly to a method and apparatus for analyzing gaseous mixtures and, more specifically, to the measurement of small concentrations of vinyl chloride in air.

Concern with the health hazards associated with industrial exposure to vinyl chloride has caused the allowable concentration of vinyl chloride to be reduced substantially from the previous standard of five hundred parts per million for continuous exposure. Analysis of vinyl chloride in industrial atmospheres at low levels approaching zero concentration has become of considerable interest. The present invention is directed primarily to a new method and apparatus for making such analyses of low concentrations of vinyl chloride in air. More broadly, the invention may be applied to analysis of other compounds as well.

Available methods for measurement of vinyl chloride in air include gas chromatography and infrared spectrometry, which are complex and quite expensive, although very sensitive to low concentrations. Other possible techniques include thermal decomposition of the compound, an example of which is given in U.S. Pat. No. 3,546,079. Simple leak detection tests in which flames are colored by the compound detected have also been applied for the relatively high concentration heretofore common, but these are not suitable for the low concentrations which are currently of interest. Thus, the present invention has as an objective providing a new, relatively simple, and inexpensive method for analysis of low concentrations of vinyl chloride in air.

SUMMARY OF THE INVENTION

In its broadest aspects, the invention includes the steps of sampling the gaseous mixture, exposing that sample to ultraviolet light of sufficient intensity to decompose certain components of interest, detecting and measuring the concentration of the decomposition products, and relating those measurements to the original composition of the sample.

As specifically applied to the measurement of low concentrations of vinyl chloride in air in industrial atmospheres, the invention includes a sample system for drawing in a representative sample of the atmosphere and introducing it into a chamber where it is exposed to ultraviolet light of such intensity as to decompose essentially all of the vinyl chloride present. Thereafter, the decomposition products are passed into an electrical conductivity instrument where the decomposition products are absorbed in deionized water and the change in electrical conductivity of the water is measured as an indirect measure of the quantity of the vinyl chloride present in the original sample.

In situations where interfering compounds are present, that is those which absorbed in water change its electrical conductivity, it has been found effective to water scrub the sample gas prior to exposing it to ultraviolet light. The water scrubbing step removes the compounds which would otherwise interfere with the electrical conductivity measurements, but does not remove a significant quantity of vinyl chloride. Later exposure to ultraviolet light will decompose the vinyl chloride and absorption in a conductivity instrument will produce an accurate measure of the vinyl chloride in the original sample.

The invention may be applied to a number of other compounds, as limited by their tendency to decompose when exposed to ultraviolet light and on the ability to remove interfering compounds and to measure the decomposition products. Alternatively, it is within the scope of the invention to decompose interfering compounds by ultraviolet radiation and to remove them in order that analysis may be made of undecomposed compounds.

BRIEF DESCRIPTION OF THE DRAWINGS

FIG. 1 is a schematic flow diagram illustrating the basic process of the invention.

FIG. 2 is a diagram of an alternate form of the invention used where interfering compounds are present.

DESCRIPTION OF THE PREFERRED EMBODIMENTS

Although the invention relates in one specific embodiment to the problem of analyzing vinyl chloride in air at relatively low concentrations, nevertheless, the invention is broadly applicable to gas analysis in a number of other situations, as will become clear in the subsequent description. However, for the most part, this discussion will be primarily related to the problem of analyzing vinyl chloride and other chemical compounds in air, as found in industrial applications of the invention.

Many times, as in polyvinyl chloride manufacturing and processing, vinyl chloride will be the principal compound present in the air and essentially no interfering compounds will be present. A schematic diagram of an application of the invention where no interfering compounds are present is given in FIG. 1. The sampling system 10 draws in a mixture of vinyl chloride and air from the surroundings at a rate suitable for subsequent processing and detection. This sample often might be conditioned by filtering, temperature adjustment, and the like, in order to improve the accuracy of the analysis. After the sample has been taken, it is transferred to the decomposition chamber 12 where the sample is exposed to intense ultraviolet radiation which converts essentially all of the vinyl chloride to decomposition products which include phosgene and hydrogen chloride. Immediately after decomposition, the sample containing decomposed vinyl chloride is passed to the detecting means 14 where the amount of decomposition products is measured and that information is converted to the quantity of vinyl chloride present in the original sample. Thereafter, the sample is exhausted from the equipment, to be replaced by a new sample.

When measuring vinyl chloride in air, several types of detectors are possible including various indicators of the acid properties of the composition products e.g., pH, colorimetric indicators. While vinyl chloride itself is only slightly soluble in water, hydrogen chloride is readily absorbed. Thus, a particularly suitable method of measuring decomposition products is to pass them into an electrical conductivity instrument where the decomposition products of vinyl chloride are absorbed in deionized water, changing its electrical conductivity in proportion to the amount absorbed. This change indicates by inference, the quantity of vinyl chloride present in the original sample.

The system is capable of measuring a vinyl chloride concentration in air below one part per million, with a minimum sensitivity of about 50 parts per billion. By simply applying conventional voltage divider circuits, it has been found possible to extend the practical analytical range upward of 25 parts per million. Beyond this, other adjustments of the variables which affect the detector capability could permit operation of an instrument with relatively high concentrations of vinyl chloride. However, the lower concentrations from 0–1 parts per million are of principal interest today.

EXAMPLE

Performance of the invention has been demonstrated by adapting a Davis Instruments Company Model 11-7000 $SO_2$ Monitor to measure vinyl chloride according to the invention. This instrument is an electrical conductivity analyzer and contains sample induction means for extracting a sample from the surrounding air, as it was designed to monitor small quantities of $SO_2$ in the ambient air. Sample flow rate was adjusted to two liters per minute and the gas was exposed for about 30 seconds to ultraviolet radiation emitted by an Ultraviolet Products 6 inch photochemical immersion lamp, Model PCQ 9G-1 mounted in a one liter flask, which delivers about two and one-half watts of radiation, about 90% of which is at 2537 Angstroms. It was found that such an exposure would decompose about 80% or more of the vinyl chloride present. It was found that the intensity of the exposure was important since with only half as much exposure, the decomposition of vinyl chloride was insufficient. The air sample containing the decomposed products was passed into the Davis conductivity detector, where it was absorbed by deionized water flowing through the absorber at 6 milliliters per minute. The change in electrical conductivity of the water was measured and related to the vinyl chloride concentration of the original sample. The lowest concentration which could be detected was 50 parts per billion of vinyl chloride in air.

While in many industrial applications, an instrument designed according to the foregoing test example will be quite satisfactory, it will be apparent that for improved accuracy under circumstances where interfering compounds are present, that it will be necessary to avoid the effect of those compounds. FIG. 2 illustrates a modification of the basic invention wherein a scrubbing system 16 is provided upstream of the decomposing step 12 in order to remove these compounds. Typically, compounds which will affect electrical conductivity may be absorbed in deionized water in scrubber 16, while permitting substantially all of the vinyl chloride to pass through. Typical of interfering compounds which may be present and which can be removed by a simple water scrubbing operation are $H_2S$, $SO_2$, and chlorine. For most situations when vinyl chloride is encountered, the sample leaving such a scrubbing step contains only vinyl chloride and air, which may be decomposed by ultraviolet radiation and detected in the same manner as discussed in FIG. 1. Also, FIG. 2 illustrates the possibility of using a sampling system 10 located downstream of the detecting means 14, rather than at the inlet of the system as was shown in FIG. 1. It will be appreciated that such a location is primarily a matter of mechanical instrument design rather than essential of the invention.

The method of the invention can also be applied to measure such compounds as carbon disulfide, hydrogen sulfide, nitric oxide, and other airborne contaminants which can be decomposed or otherwise affected by exposure to intense ultraviolet radiation. For example, nitric oxide may be oxidized to nitrogen dioxide by ultraviolet radiation, then absorbed in deionized water and measured by the change in electrical conductivity. In another example, to analyze a mixture of hydrogen sulfide, carbon disulfide, and carbonyl sulfide in air and using a sulfur compound detector instead of an electrical conductivity instrument, a sequential analysis can be carried out which will give all three compounds by scrubbing for $H_2S$ removal and exposing to ultraviolet radiation for carbon disulfide decomposition followed by additional scrubbing to remove the decomposition products, leaving only carbonyl sulfide in the gas.

The foregoing description of the preferred embodiments is for illustration of the invention only and should not be considered to limit the scope thereof which is defined by the claims which follow.

What is claimed is:

1. A method of analyzing a gaseous mixture comprising:
   a. sampling said gaseous mixture;
   b. exposing said gaseous mixture sample of (a) to ultraviolet radiation of sufficient intensity to decompose at least one predetermined component of said mixture to be analyzed and thereby provide a gaseous sample with decomposition products of said component;
   c. measuring the quantity of decomposition products in said gaseous sample from step (b) by absorbing said decomposition products in a liquid absorbent and measuring the change in electrical conductivity of said liquid absorbent with said decomposition products, and thereafter relating said measured change to the amount of said predetermined component in said sample.

2. The method of claim 1 further comprising selectively removing components of said gaseous mixture capable of interference with the measurement of (c) prior to said exposure of (b).

3. The method of claim 2 wherein interfering components are selectively removed by passing said gaseous mixture sample through an absorbing means capable of removing said interfering components while permitting substantially all of said predetermined components to be decomposed in step (c) to pass through said absorbing means.

4. The method of claim 1 wherein said gaseous mixture includes vinyl chloride as the predetermined component to be analyzed.

5. The method of claim 4 wherein the wavelength of said ultraviolet radiation is predominently 2537 Angstroms.

6. The method of claim 5 wherein the sample of (a) is exposed for about 30 seconds to ultraviolet radiation having an intensity of about 2.5 watts.

7. The method of claim 1 wherein said decomposition products are absorbed in deionized water.

8. An apparatus for analyzing a gaseous mixture comprising:
   a. sample means for separating a portion of said gaseous mixture and transferring said portion to subsequent analyzing means;
   b. ultraviolet radiation decomposing means for receiving and exposing said sample of (a) to ultraviolet radiation, thereby decomposing at least one predetermined component of said sample; and
   c. measuring means including means adapted to contain a liquid absorbent for absorbing the decomposition products resulting from (b) and to measure the change in the electrical conductivity of said liquid absorbent, and to determine the quantity of decomposition products produced by said decomposing means and to relate said changes in electrical conductivity to the amount of said predetermined component in said sample.

9. The apparatus of claim 8 further comprising absorbing means disposed before said decomposing means of (b) for removing gaseous components of said sample capable of interfering with the measurement of decomposition products by the measuring means of (c) while permitting the predetermined components to be analyzed to pass through.

10. A method of analyzing a gaseous mixture comprising:
   a. sampling said gaseous mixture;
   b. selectively removing components of said gaseous mixture capable of interfering with the subsequent measurement of predetermined other components;
   c. exposing the sample of (a) after the selective removal of interfering compounds of (b) to ultraviolet radiation of sufficient intensity to decompose other interfering components;
   d. selectively removing the interfering components decomposed in (c); and
   e. measuring the quantity of said predetermined compounds remaining in said sample subsequent to the removal of interfering compounds in (b) and (d) by absorbing said predetermined compounds in a liquid absorbent and measuring the change in electrical conductivity of said liquid absorbent with said compounds therein.

* * * * *